United States Patent [19]

Sirota

[11] Patent Number: 4,777,938
[45] Date of Patent: Oct. 18, 1988

[54] BABYSITTER TOY FOR WATCHING AND INSTRUCTING CHILD

[76] Inventor: Vladimir Sirota, 130 W. 67 St., New York, N.Y. 10023

[21] Appl. No.: 858,913

[22] Filed: May 2, 1986

[51] Int. Cl.$^4$ ............................................ A61M 21/00
[52] U.S. Cl. ...................... 600/27; 446/301; 446/342; 369/31; 600/28
[58] Field of Search .................. 128/1 C, 706, 707; 446/301, 342; 369/19, 31; 340/573, 575; 434/86

[56] References Cited

U.S. PATENT DOCUMENTS

| | | | |
|---|---|---|---|
| 2,273,836 | 2/1942 | Dale | 446/342 |
| 2,794,298 | 7/1954 | Mason | 128/1 C |
| 3,292,610 | 2/1963 | Newman | 446/301 |
| 3,712,292 | 1/1973 | Zentmeyer | 128/1 C |
| 3,720,005 | 3/1973 | Roche | 369/31 |
| 4,157,088 | 6/1979 | Gracey | 128/1 C |
| 4,282,864 | 8/1981 | Pizer | 128/1 C |
| 4,315,502 | 2/1982 | Gorges | 128/1 C |
| 4,341,035 | 7/1982 | Jaworski et al. | 446/341 |

FOREIGN PATENT DOCUMENTS 2547690  6/1984  France ............................ 128/1 C Primary Examiner—William E. Kamm
Assistant Examiner—Timothy J. Keegan

[57] ABSTRACT

A toy having an element which forms a message such that a person under its influence feels an urge to fall asleep, and a sending element which senses a signal from the person when he or she does not sleep and then activates the message forming element, so that the latter not only tells stories or fairy tales but also puts a user to sleep. One of the messages can be a lullaby. The toy can also be actuated by the pulse beat of the user, and the pulse beat data can be displayed so that the toy simultanesouly serves as a medical instrument.

18 Claims, 3 Drawing Sheets

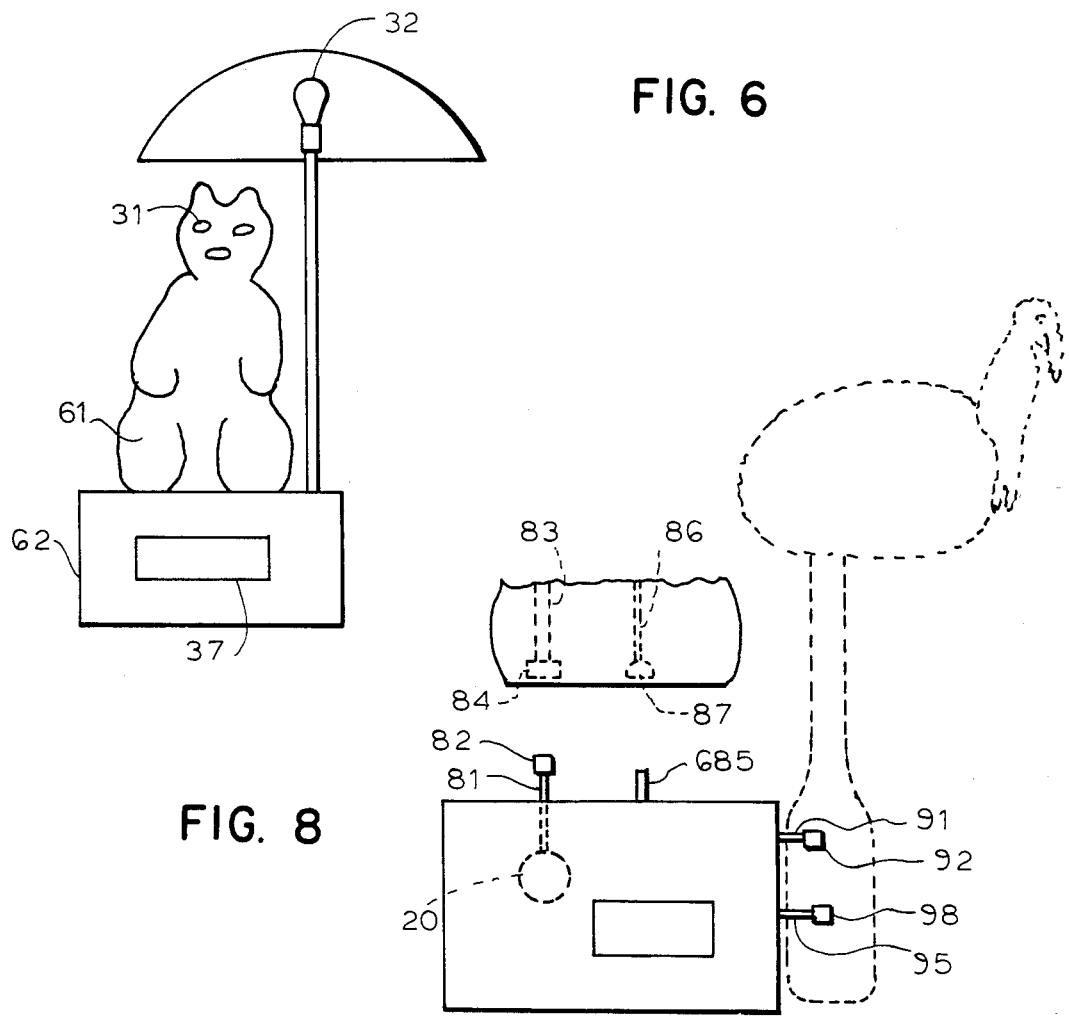
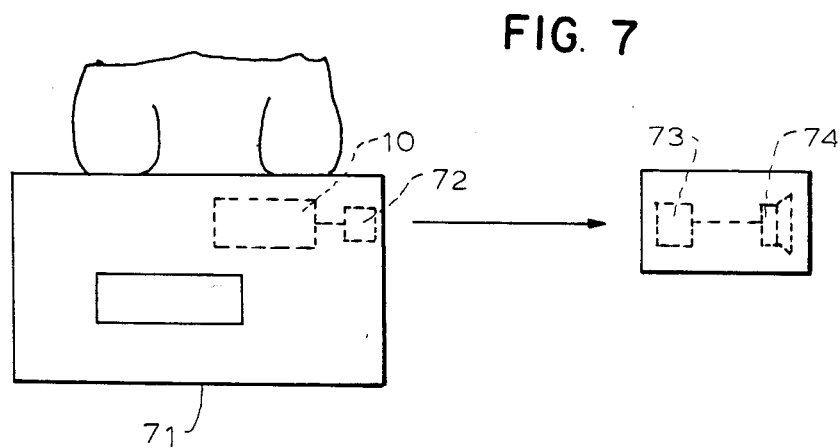

4,777,938

BABYSITTER TOY FOR WATCHING AND INSTRUCTING CHILD

BACKGROUND OF THE INVENTION

The present invention relates generally to toys.

Many toys are known in the art. There are toys which are used for urging children to fall asleep. Mainly, these toys are regular toys which are especially loved by a child such as a doll, an animal etc. With the loved toy in the bed, children feel comfortable and fall asleep faster than when they are alone in the bed. However, these toys do not deliver special messages which urge children to fall asleep, and especially when a child either has not fallen asleep or awakened again during parents attempts to put him or her asleep. Thus, it is to be understood that the effectiveness of such toys in urging children to fall asleep is very limited.

SUMMARY OF THE INVENTION

Accordingly, it is an object of the present invention to provide a toy which avoids the disadvantages of the prior art.

More particularly, it us an object of the present invention to provide a toy which is very effective in urging a person to fall asleep.

In keeping with these objects and with others which will become apparent hereinafter, one feature of the present invention resides, briefly stated in a toy which has means for sensing a signal from a person which indicates that the person does not sleep, for example the crying of a baby, and means forming a message in response to sensing the signal, for example forming an audio signal (puffing of a teddybear) and/or visual signal (closing of eyes of the teddybear).

When the toy is designed in accordance with these features, it actively senses the non-sleeping condition of a person and produces a message urging the person to fall asleep in a very effective manner.

The novel features of the present invention are set forth in particular in the appended claims. The invention itself, however, will be best understood from the following description of preferred embodiments which is accompanied by the following drawings.

BRIEF DESCRIPTION OF THE DRAWINGS

FIG. 6 shows an appearance of the toy of the present invention in accordance with one embodiment; and FIG. 7 shows another embodiment of the toy in accordance with the present invention.

FIG. 8 shows another embodiment of the toy in accordance with the present invention.

DESCRIPTION OF PREFERRED EMBODIMENTS

Figure 1:
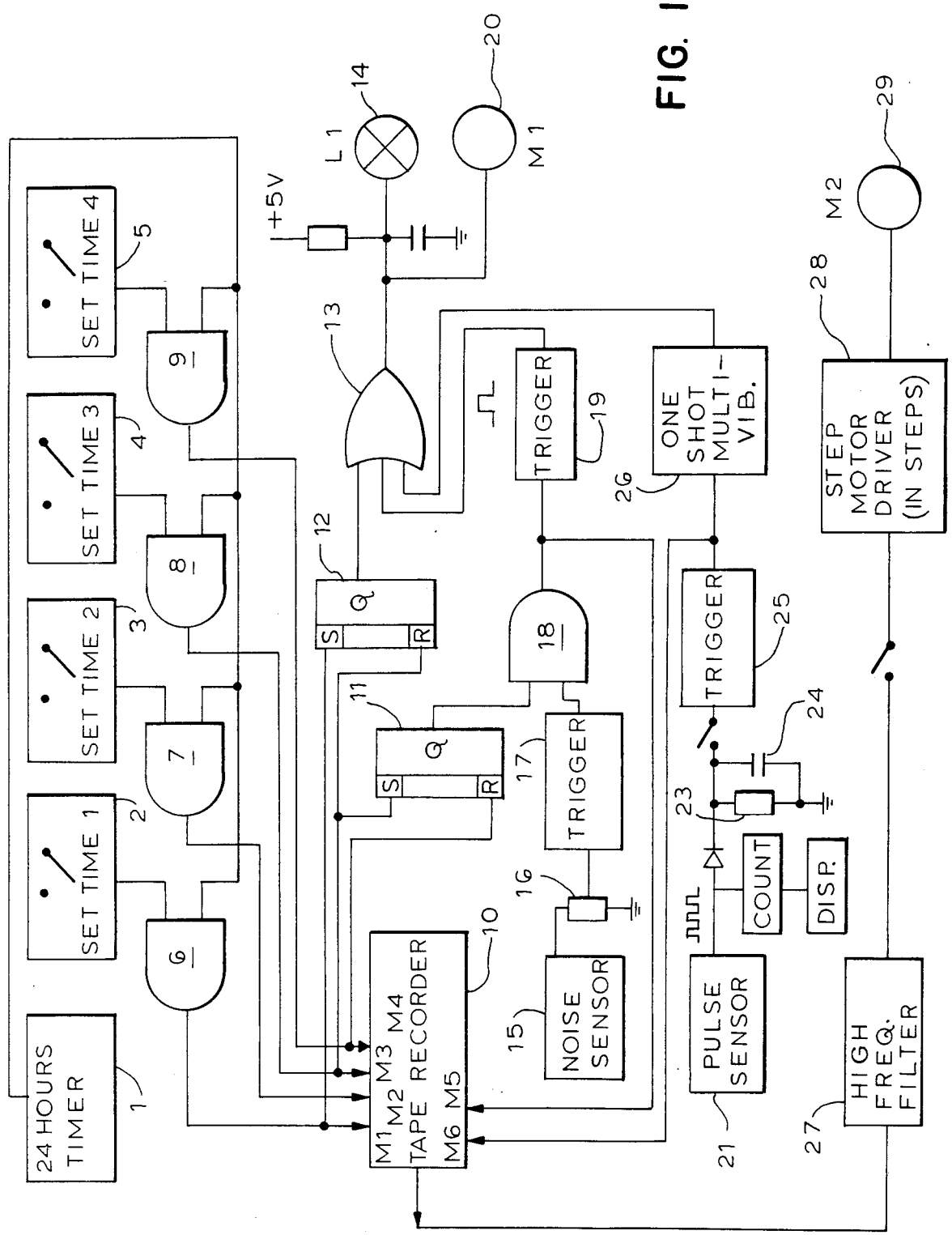
FIG. 1 is a block-diagram which schematically shows a toy in accordance with the present invention.

A toy in accordance with the present invention has a 24 hour timer identified with reference numeral 1. A plurality of time-setting devices 2-5 are further provided for setting a time for respective operations which will be explained in detail later on. The time-setting devices 2-5 are adjustable and connected to first inputs of gates "AND" 6-9, respectively. The timer 1 is connected to the second inputs of the gates "AND" 6-9. When signals of time supplied by the timer 1 coincide with the set time supplied from the time-setting devices 2-5, an output signal appears at the output of the respective gate "AND".

A device which generates sound messages is identified with reference numeral 10. It can be formed, for example, as a tape recorder. The tape recorder 10 can produce several messages, for example a message M1 which is an appeal to sleep ("sleep, baby, close your eyes" . . . ), a message M2 which is a fairy tale, a message M3 which is a puffing, a message M4 which is a welcome ("hi, how are you? did you wake up" . . . ), a message M5 which is a quieting message (be quiet, all is okay), a message M6 which is an additional fairy tale. It is to be understood that there can be more than six or less than six messages, and they can have a different content. However, there must be always a message which urges a person to fall asleep. The messages can be recorded on a revolving tape in succession after one another, they also can be recorded in a multi-track tape. In any event, the device or the tape recorder 10 must be provided with means for finding and actuating the respective message. Such tape recorders are known in the art. It is also possible to provide the tape recorder 10 with a plurality of inputs each operative for reproducing the respective message in response to receiving a signal into the respective input.

As can be seen from the drawing in FIG. 1, the "AND" gates 8 and 9 are connected with a flip-flop 11, while the "AND" gates 6 and 8 are connected with a flip-flop 12. The flip-flop 12, in turn, is connected via an "OR" gate with a light source 14 and a drive motor 20. The flip-flop 11 is connected with another input of the "OR" gate 13 via an "AND" gate 18 and a one-shot multivibrator 19. Another input of the "AND" gate 18 is connected with a person signal sensing device 15 via a sensitivity adjusting member 16 and a Schmitt trigger 17.

A person signal sensing device 15 is a device which senses a signal coming from a person, for example, a child and indicating that the child has not fallen asleep, or awakened during the process of putting him asleep or at any other time. This device can be formed as a noise sensor which produces impulses when it senses a noise for example, crying of a child. The member 16 adjusts its sensitivity and the trigger 17 sets its threshold.

The light source 14 can be arranged, for example in eyes of a toy formed as a doll, an animal or the like. It can also be formed as a lamp which is arranged on or near the toy. The eyes are identified with reference numeral 31, and the lamp is identified with reference numeral 32 in FIG. 6.

The above described part of the toy in accordance with the present invention operates in the following manner:

When the time in the respective setting device 2-5 coincides with the time supplied by the timer 1, the impulses pass through the respective "AND" gate 6-9. The tape recorder 10 finds the respective message and reproduces the same. When the message M1 is reproduced, the flip-flop 12 assumes the position "1", the light source 14 is turned on, and the motor 20 is also turned on. The tape recorder reproduces for example the appeal to sleep (M1), the light of the lamp is lit, and the eyelids move. After a certain time the impulses are supplied through the gate 7 and the message M2 is reproduced to tell a fairy tale. Then, after another time period the impulses are supplied through the gate 8 and the message M3 is reproduced which imitates puffing, for example of a teddybear toy. This succession of messages M1, M2, M3 acts upon a child in a manner which makes him or her very sleepy and finally they fall asleep. Moreover, the lamp 14 is on only for a certain time, and then it is off. The motor 20 is also off after a certain time. And, the message M3 also stops after a certain time.

It is also possible that the level of light of the lamp 14 gradually decreases. A resistor 33 and a capacitor 34 provide this gradual decrease. It is, however, possible that after a gradual decrease of light level, the lamp 14 still remains on, being supplied from a separate light power source 35. In the morning, for example, when a child has to wake up, the impulses pass through the gate 9 and the message M4 which welcomes the child, is reproduced.

When the message M3 is reproduced, the flip-flop 11 is set to the position "1" and holds it between the messages M3 and M4. If a child has not fallen asleep or awakened and cries, the noise sensor 15 senses the noise and supplies the impulses to the "AND" gate 18 which pass through this gate. As a result of this, the lamp 14 is again turned on and the motor 20 again moves the eyelids or the like. At the same time, the impulses are supplied to the tape recorder to reproduce the quieting message M5. Thus, the child who woke up again sees the light, the movement of the eyelids, and hears the quieting message, which calm him down and puts him asleep.

In accordance with the invention, a child can listen to a message, such as an additional fairy tale, by actuating this in response to his pulse beat. A pulse beat sensor is identified with reference numeral 21 and can be formed as a sensor in which a child inserts his or her finger. Upon insertion, the sensor 21 supplied impulses through a resistor-capacitor unit 23, 24, a trigger 25 and a one-shot multi-vibrator 26 to the lamp 14, the motor 20 and the input which reproduces the message M6 which is the additional fairy tale. The impulses are then supplied through a high-frequency filter 27 to a step motor driver 28 and then to a step motor 29. The step motor 29 moves a plurality of pictures which illustrate the fairy tale of message M6.

Figure 4:
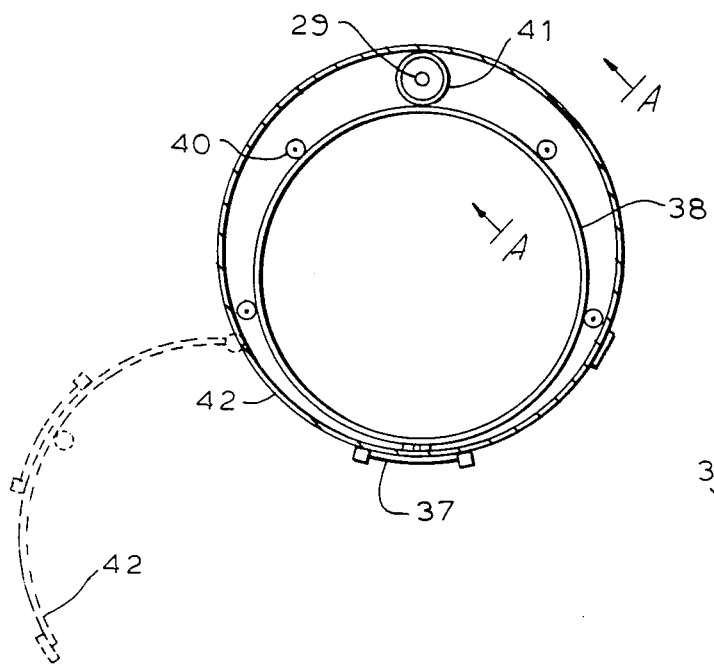
FIGS. 4 and 5 are views showing a unit for exhibiting pictures in accordance with the present invention in a plan view and in a section view, respectively.
Figure 5:
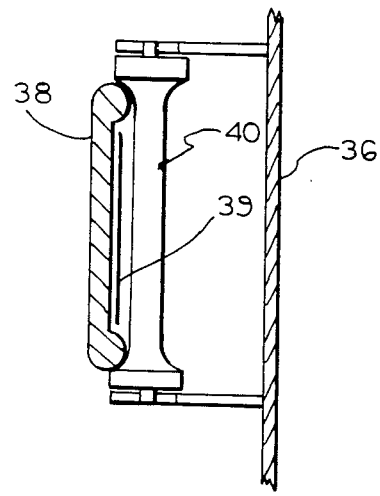

A unit for showing the pictures is shown in FIGS. 4 and 5. It has a cylindrical housing 36 with a window 37. The pictures are attached to the outer surface of the drum 38 and identified with reference numeral 39. The drum has rollers 40 and is rotated under the action of friction from a roll 41 mounted on a shaft of the motor 29. A pivotable door 42 is provided for exchange of the pictures.

Figure 2:
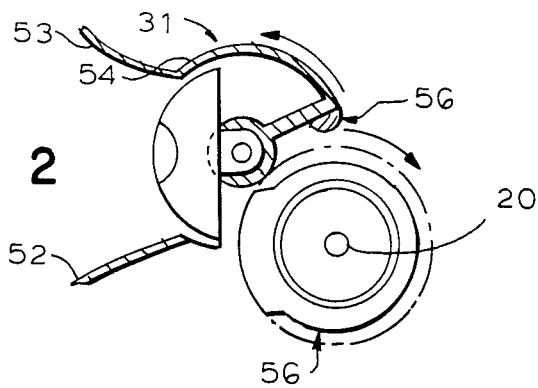
FIGS. 2 and 3 are views showing an eye unit of the toy in accordance with the present invention, with eyes open and eyes closed, respectively.
Figure 3:
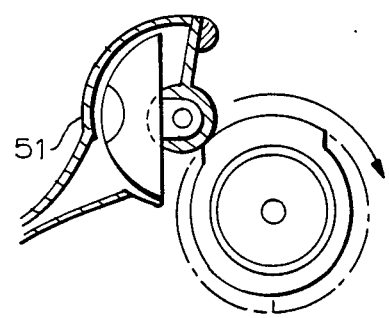

FIGS. 2 and 3 show an eye unit of the toy, for each eye. The unit has an eye provided with a light source for example a small lamp, or light emitting diodes 51. A lower eyelid 52 is stationary, while an upper eyelid 53 is attached to a pivotable arm 54 provided with a counterweight 55. The motor 20 carries a cam 56 which during its rotation acts upon the arm 54 and thereby closes and opens the upper eyelid 53.

As can be seen from FIG. 6, the toy includes a part 61 which is formed as a living being, such as a doll, and animal etc. The part 61 is arranged on a support part 62, so as to imitate sitting of the doll, the animal and the like, on the support. The picture showing unit is located in the support part 62. The tape recorder and other electronic means can also be arranged in the support part 62, while just a sound-emitting part such as a dynamic of the tape recorder can be arranged in the region of a mouth in the part 61.

FIG. 7 shows a different modification, in a schematic manner. All electronic means including the tape recorder 10 are arranged in a housing 71 which can be installed at any location, remote from a person, a child and the like. The tape recorder is provided with a transmitter 72. A receiver 73 which operates a second audio output 74 forms another small unit which can be located far from the housing 71. The receiver 73 can be connected with the transmitter 72 in a known wireless manner. The small unit 73,74 can be inserted into a pillow, put under the pillow, into a bed, etc. This is very convenient since the unit 73,74 can be located very close to the child. Also, the operation of the toy, namely its messages, can be heard only by the child and do not disturb other people.

A further important feature of the present invention is related to the pulse sensor 15. It was shown that by means of the sensor 15 a child can activate the sound or visual messages in response to his or her pulse beats. As shown in FIG. 1, the pulse sensor is connected with a counter and a display which counts and displays the data of the pulse beat of a child. Therefore the toy simultaneously serves as a medical instrument, by means of which the pulse beat of a user, for example a child, or another person, for example his or her parents can be determined and displayed.

The pulse beat sensor 21 is connected with the adjusting element 23. By means of the adjusting element 23 the threshold of sensitivity of the pulse beat sensor can be adjusted. In other words, the toy can be adjusted so that the respective message is actuated only by the pulse beat of a child, which is for example higher than the pulse beat of adults, such as his or her parents. This makes the inventive toy especially attractive and amusing. The child suggests his or her parent to actuate the toy, the parent tries but the parent's pulse beat is lower than the adjusted threshold and the respective message is not actuated. Then the child suggests the parent to exercise a little bit. After the exercising, which by the way will be good for the parent's health, the pulse beat of the parent intensifies and reaches the adjusted threshold. Now when the parent touches the pulse beat sensor, his or her pulse beat actuates the respective message of the toy in accordance with the present invention. Everybody is happy, and the toy is now simultaneously a game between children and parents, as well as a stimulator for exercising.

FIG. 8 illustrates still a further embodiment of the invention. A body part which can be formed as a doll, an animal or the like can be removed from a support and replaced by a new or different one, which for example is more attractive for each particular user. The motor 20 which actuates the eyelids, the mouth and the like to perform mechanical movements is connected with the above parts via a flexible shaft having two connectable and disconnectable portions 81 and 83 which for example are provided with a plug 82 having outer splines and socket 84 having inner splines. The light source, such as a lamp, light-emitting diode and the like is also connectable with and disconnectable from a current source for example by a conduit 86 having a socket 87 and a conduit 85 having a plug 88. When the body is installed on the support, the mechanical connection 81-84 and the electrical connection 85-88 are established and the above elements serve simultaneously for fixing the body on the support. Finally, an additional shaft portion 91 with a plug 92 and an additional conduit 95 with a plug 98 can be provided for attaching additional elements of the toy on the same principle.

The invention is not limited to the details shown since various modifications are possible. What is desired to be protected is set forth in the appended claims.

What is claimed is:

1. A babysitter toy for watching a child during an unlimited time period, comprising:
   (a) message producing means for producing a plurality of different behavioral messages and child instructional messages;
   (b) activating means for initiating operation of the message producing means;
   (c) condition sensing means for sensing at least one condition of a child and, responsive thereto, causing the activating means to activate the message producing means to produce an instructional message;
   (d) a clock timer for programming said plurality of child behavioral messages and for causing said activating means to activate the message producing means to produce different child behavioral messages; and
   (e) means for recording said child behavioral messages.

2. The invention of claim 1, wherein said condition sensing means senses an awakened condition of a child and causes activation of said activating means for activating said message producing means to produce a message to cause said child to go back to sleep.

3. The invention of claim 2, wherein the message producing means produces a visual message.

4. The invention of claim 3, wherein the visual message comprises a light which dims in intensity over a period of time.

5. The invention claim 4, wherein the message producing means produces a light which dims in intensity but does not completely extinguish.

6. The invention of claim 2, wherein the message producing means produces an audio message and a visual message.

7. The invention of claim 1, wherein the message producing means produces a "Go to sleep" visual message, and further comprising a toy figure connected to the message producing means, the "Go to sleep" visual message being transmitted by the toy figure.

8. The invention of claim 1, wherein the condition sensing means senses a pulse condition of the child.

9. The invention of claim 8, wherein the condition sensing means comprises means for visually displaying the pulse condition of the child.

10. The invention of claim 8, wherein the condition sensing means is adjustable to respond to a pulse condition within a desired range of pulses.

11. The invention of claim 8, wherein the condition sensing means responds only to a pulse condition of a child within a normal range of pulses of a child, and does not respond to a pulse condition of an adult within a normal range of pulses of an adult.

12. The invention of claim 11, wherein the condition sensing means senses a pulse condition of an adult after the adult has exercised to increase their pulse rate.

13. The invention of claim 7, further comprising support means for alternatively supporting any one of a plurality of toy figures of diverse outward appearances.

14. The invention of claim 13, further comprising an additional message producing means located remotely from said support means, and means communicating signals from said support means to said additional message producing means.

15. The invention of claim 1, wherein the condition sensing means senses a physical condition of a child, and further comprising display means connected with the condition sensing means to display the physical condition of a child sensed by the condition sensing means.

16. The invention of claim 1, wherein the condition sensed is a pulse condition and the condition sensing means senses the pulse condition within a predetermined range of pulses and does not sense the pulse condition outside of the predetermined range of pulses.

17. The invention of claim 11, wherein the condition sensing means senses a pulse condition of an adult with an abnormally high pulse rate.

18. The invention of claim 1, wherein said clock timer is connected with said activating means so as to actuate said activating means and therefore initiate operation of the message producing means at a predetermined time.

* * * * *